United States Patent
Ahmed et al.

(10) Patent No.: US 11,517,252 B2
(45) Date of Patent: Dec. 6, 2022

(54) USING A HEARABLE TO GENERATE A USER HEALTH INDICATOR

(71) Applicant: InvenSense, Inc., San Jose, CA (US)

(72) Inventors: Jibran Ahmed, Calgary (CA); Karthik Katingari, Milpitas, CA (US); Nicolas Sauvage, San Jose, CA (US)

(73) Assignee: INVENSENSE, INC., San Jose, CA (US)

( * ) Notice: Subject to any disclaimer, the term of this patent is extended or adjusted under 35 U.S.C. 154(b) by 923 days.

(21) Appl. No.: 16/265,918

(22) Filed: Feb. 1, 2019

(65) Prior Publication Data

US 2019/0231253 A1 Aug. 1, 2019

Related U.S. Application Data

(60) Provisional application No. 62/624,834, filed on Feb. 1, 2018.

(51) Int. Cl.
| | |
|---|---|
| *A61B 5/00* | (2006.01) |
| *A61B 5/11* | (2006.01) |
| *H04R 1/10* | (2006.01) |
| *H04R 3/00* | (2006.01) |
| *H04R 1/40* | (2006.01) |

(52) U.S. Cl.
CPC .......... *A61B 5/4542* (2013.01); *A61B 5/1114* (2013.01); *A61B 5/6817* (2013.01); *A61B 5/742* (2013.01); *H04R 1/1016* (2013.01); *H04R 1/406* (2013.01); *H04R 3/005* (2013.01)

(58) Field of Classification Search
CPC ... A61B 5/1114; A61B 5/4542; A61B 5/6817; A61B 5/6898; A61B 5/742; H04R 1/1016; H04R 1/406; H04R 3/005
See application file for complete search history.

(56) References Cited

U.S. PATENT DOCUMENTS

| | | | | |
|---|---|---|---|---|
| 4,836,218 | A * | 6/1989 | Gay .......................... | G01H 1/00 600/595 |
| 2007/0088544 | A1* | 4/2007 | Acero ..................... | G10L 21/02 704/226 |
| 2014/0093093 | A1* | 4/2014 | Dusan .................... | H04R 3/005 381/74 |

(Continued)

*Primary Examiner* — Christian Jang
*Assistant Examiner* — Anna Roberts
(74) *Attorney, Agent, or Firm* — Morris Patent Law, P.C., L.L.O.

(57) ABSTRACT

A hearable comprises at least one microphone coupled with a wearable structure and a sensor processing unit disposed within the wearable structure and coupled with the microphone. A portion of the wearable structure is configured to be disposed within a user's ear. The sensor processing unit acquires audio data from the at least one microphone and head motion data from at least one motion sensor of the sensor processing unit. The head motion data describes motions of the user's head and comprises cranium motion data and mandible motion data. The sensor processing unit separates the mandible motion data from the head motion data, synchronizes the mandible motion data and the audio data into a synchronized data stream; classifies an activity of the head during a portion of the synchronized data stream; and generates a health indicator for the user based on the activity and the synchronized data stream.

25 Claims, 5 Drawing Sheets

(56) References Cited

U.S. PATENT DOCUMENTS

| | | | | |
|---|---|---|---|---|
| 2014/0251023 A1* | 9/2014 | Magomedov | .......... | A61B 5/228 |
| | | | | 73/779 |
| 2016/0187654 A1* | 6/2016 | Border | .................... | G02B 5/18 |
| | | | | 359/567 |
| 2016/0353195 A1* | 12/2016 | Lott | .................... | H04W 12/065 |
| 2017/0000430 A1* | 1/2017 | Lu | .......................... | A61B 6/032 |
| 2018/0242908 A1* | 8/2018 | Sazonov | .............. | A61B 5/7278 |

* cited by examiner

500

ACQUIRING, BY A SENSOR PROCESSOR OF A HEARABLE, AUDIO DATA FROM A MICROPHONE OF A HEARABLE DISPOSED AT LEAST PARTIALLY WITHIN AN EAR OF A USER OF THE HEARABLE
510

ACQUIRING, BY A SENSOR PROCESSOR OF THE HEARABLE, HEAD MOTION DATA FROM AT LEAST ONE MOTION SENSOR OF THE HEARABLE WHILE THE HEARABLE IS DISPOSED AT LEAST PARTIALLY WITHIN THE EAR OF THE USER, WHEREIN THE HEAD MOTION DATA DESCRIBES MOTIONS OF A HEAD OF THE USER, WHEREIN THE HEAD COMPRISES A CRANIUM AND A MANDIBLE, AND THE HEAD MOTION DATA COMPRISES CRANIUM MOTION DATA AND MANDIBLE MOTION DATA
520

SEPARATING, BY THE SENSOR PROCESSOR, THE MANDIBLE MOTION DATA FROM THE HEAD MOTION DATA
530

SYNCHRONIZING, BY THE SENSOR PROCESSOR, THE MANDIBLE MOTION DATA AND THE AUDIO DATA INTO A SYNCHRONIZED DATA STREAM
540

CLASSIFYING, BY THE SENSOR PROCESSOR, AN ACTIVITY OF THE HEAD DURING A PORTION OF THE SYNCHRONIZED DATA STREAM
550

GENERATING, BY THE SENSOR PROCESSOR, A HEALTH INDICATOR FOR THE USER BASED ON THE ACTIVITY AND THE SYNCHRONIZED DATA STREAM
560

FIG. 5

USING A HEARABLE TO GENERATE A USER HEALTH INDICATOR

CROSS-REFERENCE TO RELATED APPLICATION—PROVISIONAL

This application claims priority to and benefit of U.S. Provisional Patent Application No. 62/624,834 filed on Feb. 1, 2018 entitled "HEARING INSTRUMENTS COMPRISING MOTION SENSORS" by Karthik Katingari et al., and assigned to the assignee of the present application, the disclosure of which is hereby incorporated herein by reference in its entirety.

BACKGROUND

A hearing instrument (HI), also referred to as a hearing aid or "hearable," is a device designed to reproduce sound from a recorded source and/or improve hearing by making sound audible to a person with hearing loss. A hearable may or may not be a medical device. In some embodiments, hearable which is not a medical device may be an enhanced headphone which is used for listening to phone calls, music, and the like provided to the hearable via communication with an electronic device. A hearable in general comprises a microphone and speaker combination, along with a processor to process the signal captured by the microphone and to control the output of the speaker. A hearable may include additional features such as, for example touch sensors, which permit additional functionality. A hearable may also be coupled (typically wirelessly) with another hearable and/or an electronic device such as a computer, smartphone, smartwatch, or a tablet computer.

BRIEF DESCRIPTION OF DRAWINGS

The accompanying drawings, which are incorporated in and form a part of the Description of Embodiments, illustrate various embodiments of the subject matter and, together with the Description of Embodiments, serve to explain principles of the subject matter discussed below. Unless specifically noted, the drawings referred to in this Brief Description of Drawings should be understood as not being drawn to scale. Herein, like items are labeled with like item numbers.

FIG. 5 illustrates a flow diagram of an example method of hearable use, in accordance with various aspects of the present disclosure.

DESCRIPTION OF EMBODIMENTS

Figure 1:
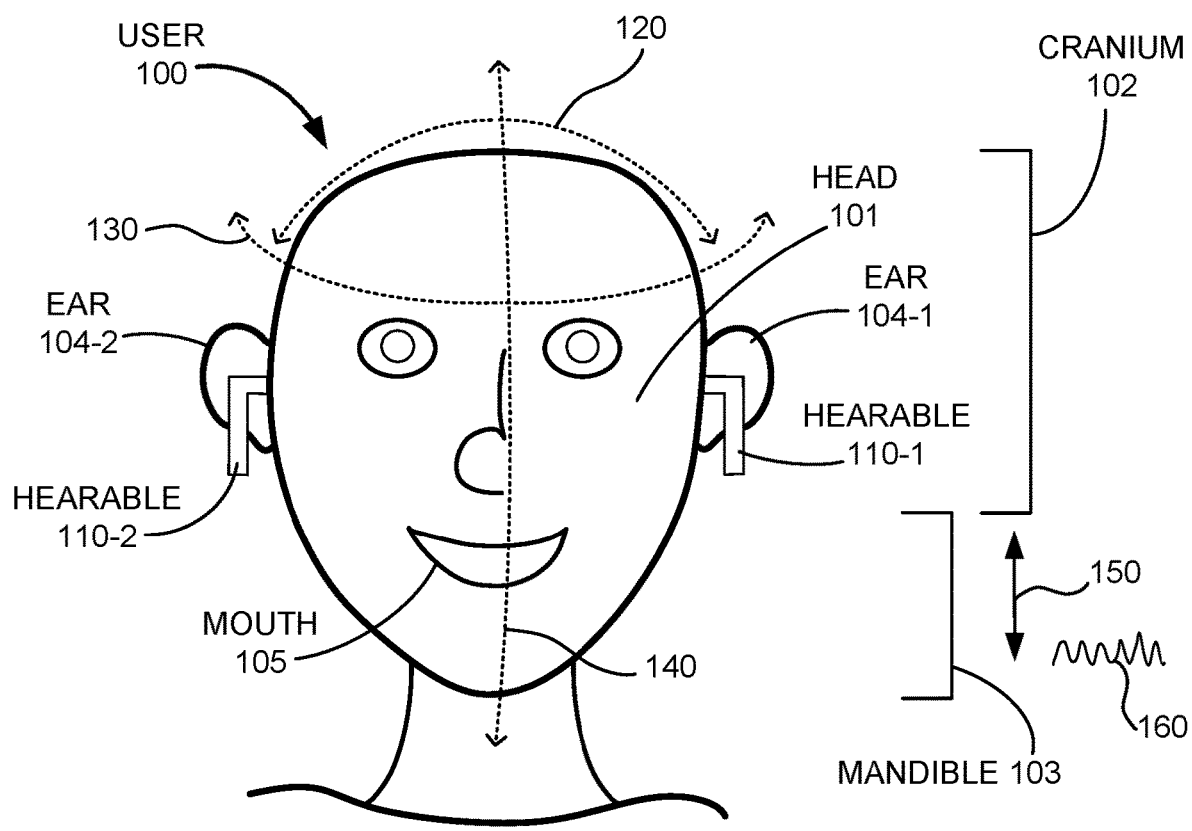
FIG. 1 shows a diagram of a human user wearing a pair of hearables in the ears of the user, in accordance with various aspects of the present disclosure.

Reference will now be made in detail to various embodiments of the subject matter, examples of which are illustrated in the accompanying drawings. While various embodiments are discussed herein, it will be understood that they are not intended to limit to these embodiments. On the contrary, the presented embodiments are intended to cover alternatives, modifications and equivalents, which may be included within the spirit and scope the various embodiments as defined by the appended claims. Furthermore, in this Description of Embodiments, numerous specific details are set forth in order to provide a thorough understanding of embodiments of the present subject matter. However, embodiments may be practiced without these specific details. In other instances, well known methods, procedures, components, and circuits have not been described in detail as not to unnecessarily obscure aspects of the described embodiments.

Overview of Discussion

A variety of uses of hearables are described which add or extend the functionality of hearables in ways which quantify the health of a user of the hearable(s). In addition to the typical speaker, microphone, and processor, the described hearables include additional sensors, such as motion sensors (e.g., accelerometers, gyroscopes, magnetometers, inertial sensors, and/or pressure sensors) and, in some embodiments, one or more additional microphones. The additional sensors may improve the performance of the hearable and/or provide additional functionalities. This disclosure discusses functionalities that can be added to the hearable(s) by using the hearable(s) for acquiring head motion data and analyzing it alone or in combination with audio data acquired with the hearable(s). For example, analyzing data acquired via the hearable(s) facilitates generating one or more health indicators for the user which can be used to rate or compare an aspect of the user's health to a standard or benchmark or to one or more previously generated health indicators for the user.

Discussion begins with a description of notation and nomenclature. Discussion continues with description of a diagram of a human user wearing a pair of hearables in the ears of the user. An example hearable its components are described. Finally, operation of a hearable (or pair of hearables), and components thereof, is discussed in conjunction with description of an example method of hearable use.

Notation and Nomenclature

Some portions of the detailed descriptions which follow are presented in terms of procedures, logic blocks, processes, modules and other symbolic representations of operations on data bits within a computer memory. These descriptions and representations are the means used by those skilled in the data processing arts to most effectively convey the substance of their work to others skilled in the art. In the present application, a procedure, logic block, process, module, or the like, is conceived to be one or more self-consistent procedures or instructions leading to a desired result. The procedures are those requiring physical manipulations of physical quantities. Usually, although not necessarily, these quantities take the form of electrical or magnetic signals capable of being stored, transferred, combined, compared, and otherwise manipulated in an electronic device/component.

It should be borne in mind, however, that all of these and similar terms are to be associated with the appropriate physical quantities and are merely convenient labels applied to these quantities. Unless specifically stated otherwise as apparent from the following discussions, it is appreciated that throughout the description of embodiments, discussions utilizing terms such as "acquiring," "separating," "synchronizing," "classifying," "generating," "determining," "adjusting," "filtering," "using," "comparing," or the like, refer to the actions and processes of an electronic device or component such as: a hearable, a pair of hearables, a processor of a hearable, a sensor processing unit, a sensor processor, a memory, or the like, or a combination thereof. The electronic device/component manipulates and transforms data represented as physical (electronic and/or magnetic) quantities within the registers and memories into other data similarly represented as physical quantities within memories or registers or other such information storage, transmission, processing, or display components.

Embodiments described herein may be discussed in the general context of processor-executable instructions residing on some form of non-transitory processor-readable medium, such as program modules or logic, executed by one or more computers, processors, or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, circuits, and steps have been described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the example electronic device(s) described herein may include components other than those shown, including well-known components.

The techniques described herein may be implemented in hardware, or a combination of hardware with firmware and/or software, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, cause a processor and/or other components to perform one or more of the methods described herein. The non-transitory processor-readable data storage medium may form part of a computer program product, which may include packaging materials.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), flash memory, other known storage media, and the like. The techniques additionally, or alternatively, may be realized at least in part by a processor-readable communication medium that carries or communicates code in the form of instructions or data structures and that can be accessed, read, and/or executed by a computer or other processor.

The various illustrative logical blocks, modules, circuits and instructions described in connection with the embodiments disclosed herein may be executed by one or more processors, such as host processor(s) or core(s) thereof, digital signal processors (DSPs), general purpose microprocessors, application specific integrated circuits (ASICs), application specific instruction set processors (ASIPs), field programmable gate arrays (FPGAs), or other equivalent integrated or discrete logic circuitry. The term "processor," as used herein may refer to any of the foregoing structures or any other structure suitable for implementation of the techniques described herein. In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a plurality of microprocessors, one or more microprocessors in conjunction with an ASIC, or any other such configuration.

In various example embodiments discussed herein, a chip is defined to include at least one substrate typically formed from a semiconductor material. A single chip may for example be formed from multiple substrates, where the substrates are mechanically bonded to preserve the functionality. Multiple chip (or multi-chip) includes at least two substrates, wherein the two substrates are electrically connected, but do not require mechanical bonding.

A package provides electrical connection between the bond pads on the chip (or for example a multi-chip module) to a metal lead that can be soldered to a printed circuit board (or PCB). A package typically comprises a substrate and a cover. An Integrated Circuit (IC) substrate may refer to a silicon substrate with electrical circuits, typically CMOS circuits. A MEMS substrate provides mechanical support for the MEMS structure(s). The MEMS structural layer is attached to the MEMS substrate. The MEMS substrate is also referred to as handle substrate or handle wafer. In some embodiments, the handle substrate serves as a cap to the MEMS structure.

Some embodiments may, for example, comprise one or more motion sensors. For example, an embodiment with an accelerometer, a gyroscope, and a magnetometer or other compass technology, which each provide a measurement along three axes that are orthogonal relative to each other, may be referred to as a 9-axis device. In another embodiment three-axis accelerometer and a three-axis gyroscope may be used to form a 6-axis device. Other embodiments may, for example, comprise an accelerometer, gyroscope, compass, and pressure sensor, and may be referred to as a 10-axis device. Other embodiments may not include all the sensors or may provide measurements along one or more axes. Some or all of the sensors may be MEMS sensors. Some or all of the sensors may be incorporated in a sensor processing unit along with a sensor processor and disposed in a single semiconductor package.

For example, one or more sensors may, for example, be formed on a first substrate. Various embodiments may, for example, include solid-state sensors and/or any other type of sensors. The electronic circuits in sensor processing unit may, for example, receive measurement outputs from the one or more sensors. In various embodiments, the electronic circuits process the sensor data. The electronic circuits may, for example, be implemented on a second silicon substrate. In some embodiments, the first substrate may be vertically stacked, attached and electrically connected to the second substrate in a single semiconductor chip, while in other embodiments, the first substrate may be disposed laterally and electrically connected to the second substrate in a single semiconductor package, such as a single integrated circuit.

In an example embodiment, the first substrate is attached to the second substrate through wafer bonding, as described in commonly owned U.S. Pat. No. 7,104,129, to simultaneously provide electrical connections and hermetically seal the MEMS devices. This fabrication technique advantageously enables technology that allows for the design and manufacture of high performance, multi-axis, inertial sensors in a very small and economical package. Integration at the wafer-level minimizes parasitic capacitances, allowing for improved signal-to-noise relative to a discrete solution. Such integration at the wafer-level also enables the incorporation of a rich feature set which minimizes the need for external amplification.

Wear of Hearables by a User

FIG. 1 shows a diagram of a human user 100 wearing a pair of hearables 110-1, 110-2 in the ears 104-1, 104-2 of the user 100, in accordance with various aspects of the present disclosure. The wear location of a hearable 110 puts it in a near constant position and orientation with respect to the head 101/ear 104 of a user 100. Because of this, motion sensors of a hearable 110 can be used to acquire information about the movement of the head 101 of the user 100. The signals from the motion sensor comprise information about the orientation of the head and of the movement of the head. The head 101 of the user 100 includes the user's cranium 102 and the user's mandible 103 (lower jaw). The wear location of the hearable makes it possible to measure the motion and/or orientation of the cranium 102 and the mandible 103. The motion signal of the motion sensor may be a combination of the motion of the cranium and the motion of the mandible. Based on analysis of the motion signals, the motion and/or orientation of the cranium 102 and mandible 103 can be separated, as will be discuss in more detail below. The motion sensor may also detect motion of the body of the user, which may also be filtered out to determine the head motion only. The motion and orientation of the cranium 102 and the mandible 103 of the user 100 may be determined with respect to an external reference frame or may be determined with respect to each other. Motions 120, 130, and 140 are related to the cranium 102, while motion 150 is related to the mandible 103. Motion 120 is an up/down nodding or pitch motion of head 101 and in particular of cranium 102. Motion 130 is a left/right twisting or yaw motion of head 101 and in particular of cranium 102. Motion 140 is a left side to right side tilting or roll motion of head 101 and in particular of cranium 102. Motion 150 is an up/down motion of mandible 103, such as might occur during speaking or chewing with the mouth 105 of user 100. These and other motions of head 101, including vibratory motions, may be measured by and acquired from motion sensors of hearables 110. Vibratory motions may also be measured by one or more microphones in the hearable. This may be a dedicated microphone, or a microphone that is used to perform the main function of the hearable.

Description of an Example Hearable

Figure 2:
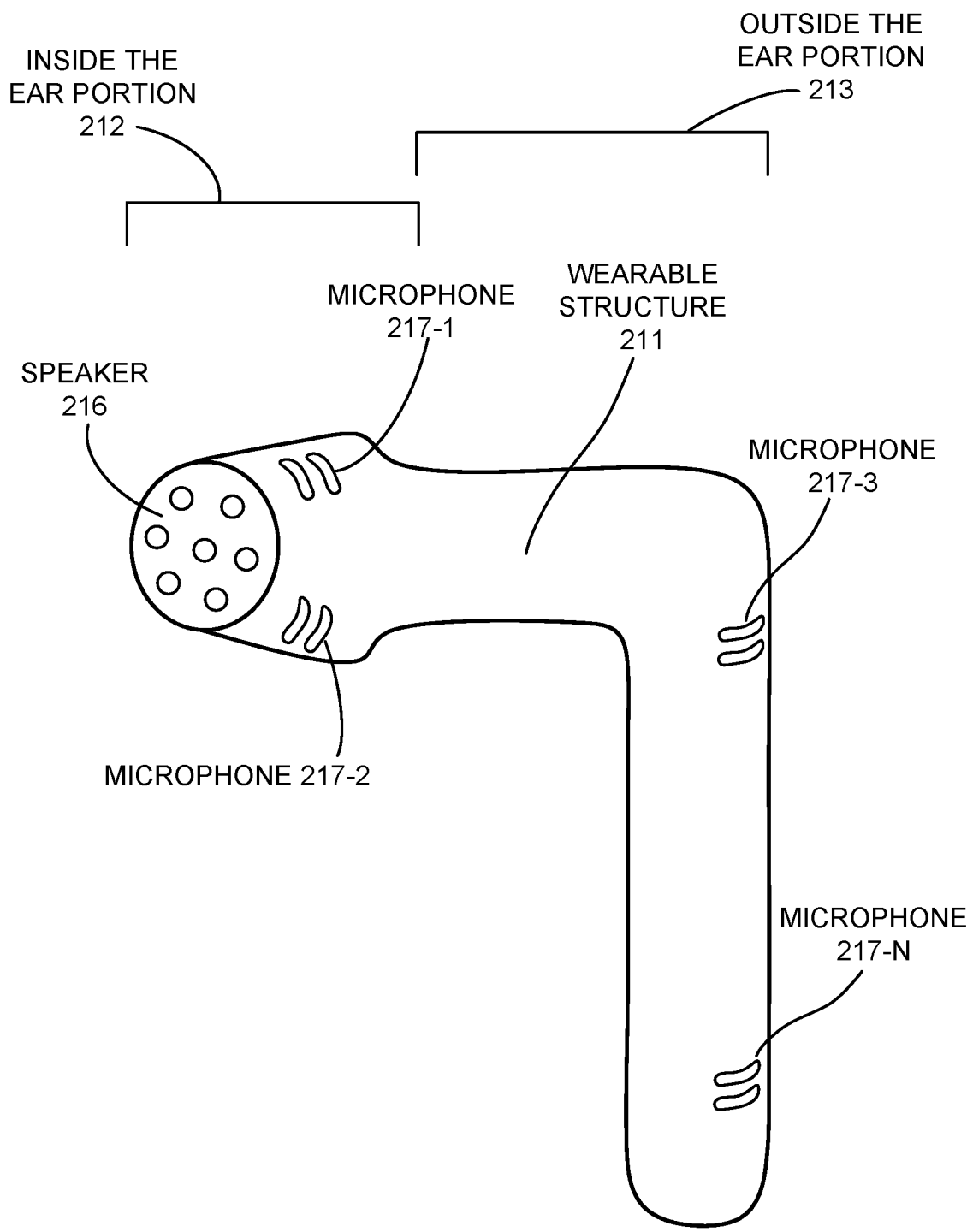
FIG. 2 illustrates the external configuration of an example hearable, in accordance with various aspects of the present disclosure.

FIG. 2 illustrates the external configuration of an example hearable 110, in accordance with various aspects of the present disclosure. This example shows only a possible configuration, formfactor, design and architecture. Many different configurations are possible, varying from embodiments where most of the device is worn outside the ear, to other embodiment that are completely worn inside the ear. Although a single hearable 110 is shown, they are often worn in pairs. Hearable 110 comprises a wearable structure 211 which is a housing for a plurality of components depicted in FIG. 2 and in FIG. 3. By "wearable" what is meant is that the outer housing of the hearable is configured to couple with an ear 104 of a user 100 such that it can be worn in the coupled state without easily coming uncoupled from the ear 104 unless the user 100 desires to remove the wearable structure 211. The coupling may include one or more of insertion into the ear canal or riding atop the ear. As depicted, wearable structure 211 includes an inside the ear portion 212 and an outside the ear portion 213. At least some, and as much as all, of inside the ear portion 212 is worn inside the ear opening/ear canal of an ear 104 of user 100. At least some, and as much as all, of outside the ear portion 213 is worn outside of the ear opening/ear canal of an ear 104 of user 100. When in use, at least a portion of hearable 110 is worn inside of the ear 104 of a user 100. Typically, this inside the ear portion 212 includes a speaker 216 or a sound tube which is coupled with the speaker 216 of the hearable. The speaker supplies audible sound for user 100 to hear. Other configurations of a hearable 110 may look different from what has been illustrated in FIG. 1 and FIG. 2 and/or may couple to an ear 104 in a different manner than illustrated but will still have a portion which resides in the ear canal/ear opening of a user 100.

As illustrated, a hearable 110 also includes one or more microphones 217. A greater or lesser number of microphones 217, than depicted, may be included in other embodiments. The microphones may be designed to pick up the frequencies of the human hearable spectrum transmitted through the air or through bone conduction, for example, to pick up vibrations transmitted through the mandible or other bone structures. Microphones 217 may be disposed on inside the ear portion 212 (e.g., microphones 217-1 and 217-2) and/or on outside the ear portion 213 (e.g., microphones 217-3 and 217-N) of hearable 110. Each microphone 217 may be a single microphone or a cluster of microphones, such as an array of three small microphones. Microphones 217-1, 217-2, or their like are configured to be disposed at least partially within the ear canal of a user 100 to acquire audio of the user 100 and to provide feedback based on the sounds generated by speaker 216. Microphones 217-3, 217-N, or their like are configured to be disposed outside of the ear canal of a user 100 to acquire audio in the environment of the user 100. Beam forming using a group of microphones 217 may be employed to locate the position of an audio source, such as a person speaking or the source of a sound, relative to the head 101 of user 100. In some instances, such beamforming may be practiced with microphones of a pair of hearables 110 which are disposed each of the ears 104 of a user 100.

Figure 3:
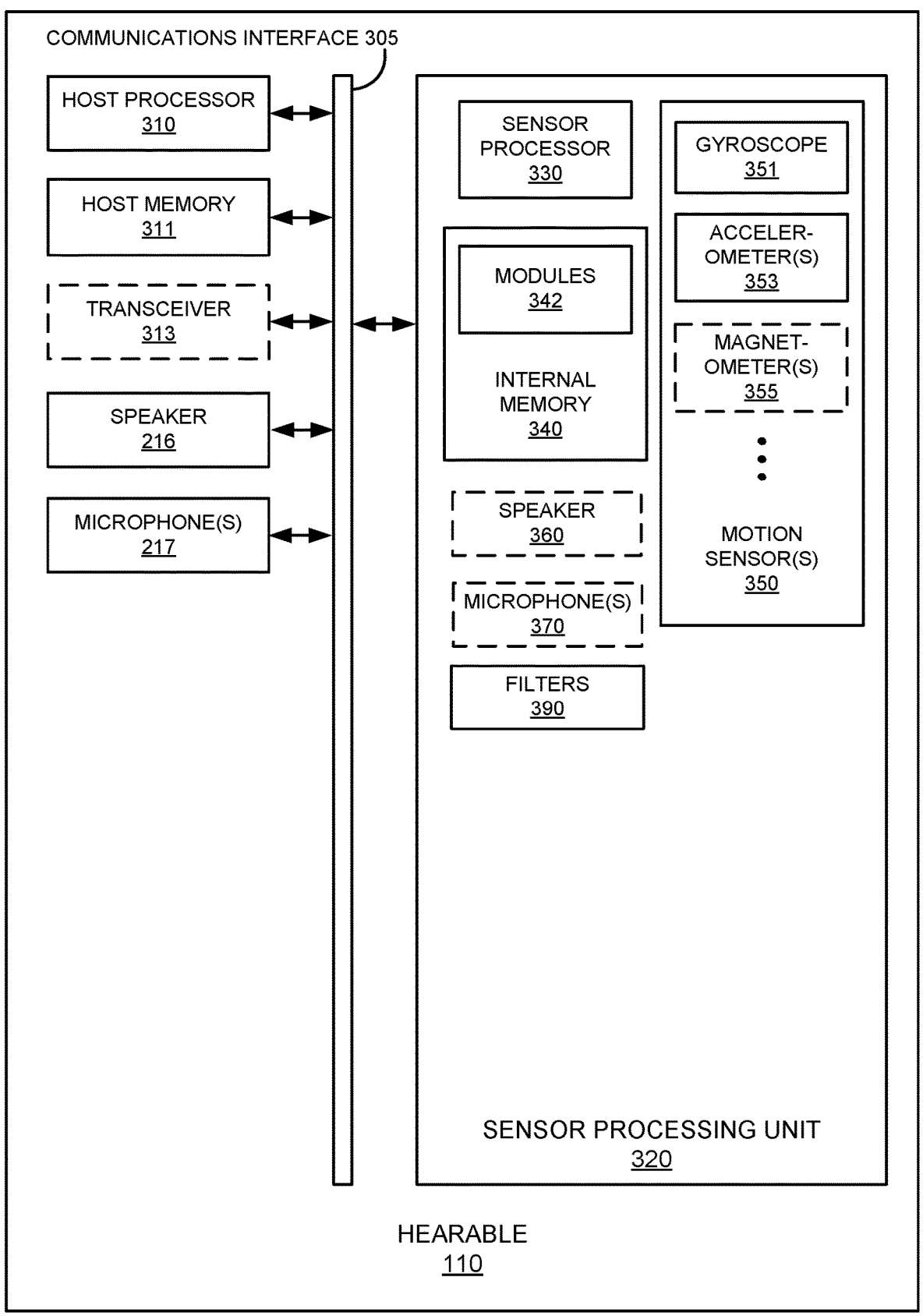
FIG. 3 shows a block diagram of components of an example hearable, in accordance with various aspects of the present disclosure.

FIG. 3 shows a block diagram of components of an example hearable 110, in accordance with various aspects of the present disclosure.

As shown, example hearable 110 comprises a communications interface 305, a host processor 310, host memory 311, at least one speaker 216, one or more microphones 217

(e.g., microphone 217-1, microphone 217-2, microphone 217-3, and/or microphone 217-N), and a sensor processing unit (SPU) 320. In some embodiments, hearable 110 may additionally include transceiver 313. As depicted in FIG. 3, included components are communicatively coupled with one another, such as, via communications interface 305.

In some embodiments, hearable 110 may be a self-contained device that performs its own operations independently of other electronic devices. However, in other embodiments, hearable 110 may function in conjunction with another electronic device such as personal computer, smartphone, smartwatch, tablet computer, another hearable 110, etc., which can communicate with hearable 110, e.g., via network connections. Hearable 110 may, for example, be capable of communicating via a wired connection using any type of wire-based communication protocol (e.g., serial transmissions, parallel transmissions, packet-based data communications), wireless connection (e.g., electromagnetic radiation, infrared radiation or other wireless technology), or a combination of one or more wired connections and one or more wireless connections.

The host processor 310 may, for example, be configured to perform the various computations and operations involved with the general function of hearable 110 (e.g., receiving audio from microphone 217-3, processing it, and supplying it to speaker 216). Host processor 310 can be one or more microprocessors, central processing units (CPUs), DSPs, general purpose microprocessors, ASICs, ASIPs, FPGAs or other processors which run software programs or applications, which may be stored in host memory 311, associated with the general and conventional functions and capabilities of hearable 110.

Communications interface 305 may be any suitable bus or interface, such as a peripheral component interconnect express (PCIe) bus, a universal serial bus (USB), a universal asynchronous receiver/transmitter (UART) serial bus, a suitable advanced microcontroller bus architecture (AMBA) interface, an Inter-Integrated Circuit (I2C) bus, a serial digital input output (SDIO) bus, or other equivalent. Communications interface 305 may facilitate communication between SPU 320 and one or more of host processor 310, host memory 311, speaker 216, and/or microphone(s) 217.

Host memory 311 may comprise programs, modules, applications, or other data for use by host processor 310. In some embodiments, host memory 311 may also hold information that that is received from or provided to sensor processing unit 320. Host memory 311 can be any suitable type of memory, including but not limited to electronic memory (e.g., read only memory (ROM), random access memory (RAM), or other electronic memory).

Transceiver 313, when included, may be one or more of a wired or wireless transceiver which facilitates receipt of data at hearable 110 from an external transmission source and transmission of data from hearable 110 to an external recipient. By way of example, and not of limitation, in various embodiments, transceiver 313 comprises one or more of: a cellular transceiver, a wireless local area network transceiver (e.g., a transceiver compliant with one or more Institute of Electrical and Electronics Engineers (IEEE) 802.11 specifications for wireless local area network communication), a wireless personal area network transceiver (e.g., a transceiver compliant with one or more IEEE 802.15 specifications (or the like) for wireless personal area network communication), and a wired serial transceiver (e.g., a universal serial bus for wired communication).

Speaker 216 may be, without limitation: a moving coil speaker, a piezoelectric speaker, or any other suitable type of speaker which converts an electrical audio signal into a corresponding emitted user audible acoustic signal (i.e., a sound). In various embodiments, speaker 216 may be capable of producing an emitted acoustic signal anywhere in the range between 20 Hz and 20 kHz. Other acoustic ranges are possible and anticipated. In some embodiments, a speaker 216 may only be functional over a portion of this acoustic range such as between 20 Hz and 15 kHz. In some embodiments, more than one speaker 216 may be included in hearable 110, and the speakers may have the same or different acoustic ranges.

A microphone 217 (including microphones 217-1, 217-2, 217-3 and 217-N) may be any type of microphone which receives an audible acoustic signal (i.e., a sound) and converts it to a corresponding electrical audio signal. A microphone 217 may comprise, without limitation, a piezoelectric microphone, a micro-electrical mechanical system (MEMS) microphone; an electrostatic microphone, or any other suitable type of microphone.

SPU 320 comprises: a sensor processor 330; internal memory 340; one or more motion sensors 350 (e.g., gyroscope 351, accelerometer 353, magnetometer 355 and/or other motion sensors such a barometric pressure sensor), and one or more filter(s) 390. In some embodiments, SPU 320 may include one or more speakers 360 and/or one or more microphones 370. In various embodiments, SPU 320 or a portion thereof, such as sensor processor 330, is communicatively coupled with host processor 310, host memory 311, and other components of hearable 110 through communications interface 305 or other well-known means. SPU 320 may also comprise a communications interface (not shown) similar to communications interface 305 and used for communications among one or more components within SPU 320.

Processor 330 can be one or more microprocessors, CPUs, DSPs, general purpose microprocessors, ASICs, ASIPs, FPGAs or other processors that run software programs, which may be stored in memory such as internal memory 340 (or elsewhere), associated with the functions of SPU 320. In some embodiments, one or more of the functions described as being performed by sensor processor 330 may be shared with or performed in whole or in part by another processor of a hearable 110, such as host processor 310.

Internal memory 340 can be any suitable type of memory, including but not limited to electronic memory (e.g., read only memory (ROM), random access memory (RAM), or other electronic memory). Internal memory 340 may store algorithms, routines, or other instructions for instructing sensor processor 330 on the processing of data output by one or more of the motion sensors 350. In some embodiments, internal memory 340 may store one or more modules 342 which may be algorithms that execute on sensor processor 330 to perform a specific function. The modules 342 may be statistical processing modules, activity detection modules, motion processing modules (e.g., a head motion processing module, a jaw bone (mandible) vibration processing module, a jaw (mandible) movement module), audio processing modules (e.g., speech recognition module, an audio thresholding module, and a beam formation/sound direction determining module), and/or decision-making modules.

Motion sensors 350, when included, may be implemented as MEMS-based motion sensors, including inertial sensors such as a gyroscope 351 or accelerometer 353, or an electromagnetic sensor such as a Hall effect or Lorentz field magnetometer 355. In some embodiments, at least a portion of the motion sensors 350 may also, for example, be based on sensor technology other than MEMS technology (e.g., CMOS technology, etc.). As desired, one or more of the motion sensors 350 may be configured to provide raw data output measured along three orthogonal axes or any equivalent structure. Motion sensor(s) 350 are communicatively coupled with sensor processor 330 by a communications interface, bus, or other well-known communication means.

A speaker 360 when included, may be any type of speaker which converts an electrical audio signal into a corresponding user audible emitted acoustic signal (i.e., a sound). In some embodiments, a speaker 360 may be based on MEMS technology. In some embodiments, more than one speaker 360 may be included, and the speakers may have the same or different acoustic ranges.

A microphone 370, when included, may be any type of microphone which receives an acoustic signal (i.e., a sound) and converts it to a corresponding electrical audio signal. A microphone 370 may comprise, without limitation, a piezoelectric microphone, a micro-electrical mechanical system (MEMS) microphone; an electrostatic microphone, or any other suitable type of microphone. In some embodiments, more than one microphone 370 may be included.

Filter(s) 390, when included, may be analog, digital, or some combination thereof. Filters 390 may include one or more of: a finite impulse response (FIR) filter, a bandpass filter, a fast Fourier transform (FFT) filter (FFT may also be performed as algorithmically by sensor processor 330). Other types of filters may additionally or alternatively be included in filters 390.

Operation of Hearable(s)

While hearables 110 are being worn by user 100, motion sensor(s) 350 of the hearables 110 may be used to pick up motion and vibrations of the mandible 103 related to the motion and sound that is produced when speaking, chewing, or swallowing and/or the up/down motion 150 of the mandible 103 when speaking, chewing, or swallowing. A single motion sensor 350 may be used to detect the vibrations and the slower motion of the mandible 103 or dedicated/specialized motion sensors 350 may be used. For example, one accelerometer 353 in a hearable 110-1 in a user's left ear 104-1 may be dedicated to detecting motion of the mandible 103 (e.g., up/down motion 150 from talking/chewing), while another accelerometer 353 in a hearable 110-2 in the user's right ear 104-2 may be dedicated to detecting and acquiring vibrations of the mandible 103 which occur due to modulation by the voice of the user 100 when talking. Head motion data may also be collected on movements of the cranium 102, such as a tilting left/right motion 120, a rotating left/right motion 130, and/or a tilting up/down motion 140. Analysis of cranium motion data and mandible motion data can be separate or combined, and either or both may be combined with the analysis of contemporaneous audio data captured by one or more microphones 217/370 of a hearable or pair of hearables. Head motion data may comprise cranium motion data and mandible motion data. In some embodiments, the cranium motion data is of interest and may be separated from, or filtered out, of the head motion data. In other embodiments, the mandible motion data is of interest and may be separated from, or filtered out, of the head motion data. The mandible motion data may be further separated into, or filtered into, mandible movement data (e.g., rotation) and mandible vibration data. The filtering may be done using, for example, frequency filtering. Other methods such as, for example, statistical feature analysis or machine learning techniques may also be used for the extraction and separation of the motion signals of interest from the head motion data. Depending on the health indicator to be determined, the cranium motion data and/or mandible motion data may be determined.

In some embodiments, speaking detection is performed by comparing the motion measured by the motion sensor (e.g., accelerometer 353) to one or more thresholds. The threshold(s) may be a preset or it may be customized for a particular user 100. If the amplitude of mandible motion data and/or mandible vibration is below the threshold(s) being used, it may be deduced that the user 100 is not speaking. If the amplitude of mandible motion data and/or mandible vibration is at or above the threshold(s) being used, it may be deduced that the user 100 is speaking. Different thresholds may be used for mandible motion and mandible vibration to classify different activities, such as e.g., speaking, eating, chewing, swallowing, teeth grinding, drinking.

In some embodiments, the speaking detection is performed by analyzing the correlation between the motion data from a motion sensor (e.g., accelerometer 353) and the audio data from one or more microphones 217/370 for the same period of time. In other words, if the microphone 217/370 detects sounds indicative of human speech, it should be analyzed if the human speech is caused by the user speaking. The microphone signal related to human speech may be compared to the mandible motion and mandible vibration, and a correlation between the microphone signal and the motion signal may be determined over a period of time covering the human speech. If there is no or little correlation, then it is determined that the user 100 is not speaking. In this case the motion sensor 350 may have measured motion not related to the speaking, but for example due to chewing or other jaw movement (which may have taken place at the same time as the human speech from another source). The correlation threshold to decide if the user is speaking may be adapted to the user, the context, and/or the type and architecture of the hearable. The determination if the user is speaking may be only based on the correlation between the motion signals and the microphone signal. Alternatively, analysis of the sound, such as e.g., frequency analysis or speech analysis, may also help determine if the sound is coming from the user, and this analysis may be combined with the speaking determination based on the motion signals. When it is determined that the user is not speaking, it may be determined that the user is listening.

In yet another embodiment, a frequency analysis may be used to separate different activities, such as listening, speaking and/or chewing. For example, the motion data may be filtered centered around frequencies of interest. Different frequency bands may be used to pick up, and either differentiate between different activities or characterize motion data in a binary fashion e.g., speaking versus not speaking (anything which does not correspond to speaking). Mandible vibration for an adult male over age 20 is typically around 100 Hz when speaking and for an adult female is typically around 200 Hz when speaking. Likewise, mandible vibration for any user is typically around 1-2 Hz for chewing and swallowing. Mandible motion data can be filtered around these frequencies, such as with bandpass filters and/or finite impulse response filters to determine when and differentiate between speaking, chewing/eating, and swallowing. The energy of the different frequency bands may be determined and compared to thresholds, which may be user dependent and/or context dependent. A time analysis or time threshold may also be used in the classification. For example, activities like speaking or chewing normally have a duration of a few seconds, while swallowing is of shorter duration. The time analysis may also be used to minimize false positives. For example, when a certain detection was made based on the motion data, but because the duration was too short, or the repetition not enough, it could be the determined class, but rather an isolation motion event.

Audio data from one or more microphones 217/370 may also be filtered, such as with a bandpass filter which captures the range of frequencies associated with speaking (e.g., a bandpass filter which passes a band of 90 to 250 Hz). The microphone(s) 217/370 may have a high bandwidth and are used to detect hearable sound spectrum and are not used to detect vibration. In some embodiments, this filtered audio data may be used independently of motion data to determine whether a user 100 is speaking or not speaking. In other embodiments, this filtered audio data may be synchronized in time with filtered motion data to determine whether both sets of data indicate a person is speaking. Synchronization may be accomplished in a variety of ways, including via time stamps collected with the capture of each type of data and via collecting and processing the data substantially at the same time. In some embodiments, when the synchronized motion data and audio data correlate, a user 100 is determined to be speaking otherwise they are determined not to be speaking. In this case, if human speech, or other sounds, are detected when the user is not speaking, it may be determined that the user is listening. An audio threshold may be used to remove sounds that have a too low amplitude.

Any of the methods and or techniques known to the person skilled in the art may be used for the activity detection. In some embodiments, the various classification settings, such as e.g., motion thresholds or frequency threshold, may be preset. The presets may be adaptive to the user 100. In some embodiments, machine learning techniques may be applied. In an initialization/learning stage, the user 100 may be asked to perform certain action, and the motion data may be analyzed to create the classification rules. For example, custom thresholds may be created by acquiring motion data during an initialization stage when the user 100 is instructed to speak. While speaking mandible motion data and/or mandible vibration data (and a frequency range and threshold amplitude and/or audio data (and a frequency range and threshold amplitude) which are associated with speech by user 110 can be acquired by motion sensors 350 of hearable 110, and one or more motion thresholds established. Similarly, (motion) thresholds, frequency setting, and other parameters may be determined for other activities using initialization/learning stages. The machine learning may be applied for the user in question or may be performed using crowd sourcing techniques. In the latter, the setting for the user may be based on setting from other/similar users. These machine learning techniques would be known to the person skilled in the art and could be easily applied or adapted for the current application.

Based on the analysis of mandible motion 150 and/or mandible vibrations, alone, or in combination with the audio data, it can be determined when and for what length of time the user 100 is speaking and when and for what length of time the user 100 is merely hearing/listening. The speaking versus listening data may be analyzed to extract one or more health indicators. The term "health" may refer to social health, mental or physical health. A health indicator may be useful for the monitoring of the health of elderly people. For example, a social health indicator may give an indication of the social interactions of a user, and a physical health indicator may be used as an indication of how well the user can hear or follow a conversation. An example health indicator is a speaking versus listening ratio. This ratio may be determined and then used as a social health and/or mental health indicator for the user 100. This speaking/listening ratio may be used to derive a social health index/status. The speaking/listening ratio may be instantaneous or cumulative. By "instantaneous" it is not meant that the ratio must be calculated right way after acquisition of data, but rather that it is for a small instant of time associated with the time period for which data is captured. This time period may be a few seconds, many minutes, or hours, or days. For example, an instantaneous health indicator may cover a one-week period. By cumulative, what is meant is that a plurality of the instances of speaking or not speaking are cumulated and the ratio is calculated from a plurality of time periods during which motion data and/or audio data were analyzed to determine if the user 100 was speaking or not speaking (e.g., hearing/listening). The cumulative health indicator may thus be a compilation of instantaneous health indicators, which may be the same instantaneous health indicators from different points in time, or different health indicators. The time span of "instantaneous" and "cumulative" may vary depending on the user, the application, and or the context. However, the use of these terms is to indicate that the "instantaneous" health indicator is based on analysis that spans a shorter time than the analysis for the "cumulative" health indicator. Correlation between the health indicators and the activities/habits of the user may also exist. Different users have different social activities, with different durations, occurrences, and repetitions. In some embodiments, a speech recognition module may be used. In its simplest form, the speech recognition module can identify when a sound is representative of human speech, but can do no further analysis. In some embodiments, the speech recognition module may be able to analyze what is being said, or if things are being repeated. Repetition in speaking and/or listening may also be used as a health indicator. For example, when someone's hearing capacity declines, a person speaking to the user often has to repeat his- or herself.

Another aspect that may be taken into account in the speaking/listening analysis, is how the user focuses on sound sources. For example, it may be determined how the user moves the head towards a sound source. Using the microphones of the hearable, the direction of the sound source may be determined, and then it may be analyzed how the user moves the head in the direction of the sound source. It is normal behavior for people to look in the direction of the sound source, for example, when in a conversation with someone, or when being addressed. Any change in behavior may be used as a health indicator, for example, of decreased hearing or mental capacity. The angle of direction of the sound source with respect to the user may be determined, and then compared with the rotation angle of the head of the user. This analysis may be triggered at the initiating of a sound source, for example when someone starts speaking or specifically addressed the user.

In some embodiments, when the source of a sound is located and a user is not oriented toward the source a triggering mechanism such as haptic feedback (e.g., buzzing of the hearable 110 in one ear 104) or audible feedback (e.g., "look left," "look up" "look right") may be provided to direct head orientation toward a sound source. Consider someone crossing the road and ambulance or car is approaching with a honk, a categorical sound detection and no response from the user may force a triggering mechanism to draw the attention of user towards sound source.

In some embodiments when a user 100 is classified as listening, voice recognition may be utilized to determine if the speaker repeats words, phrases, or sentences to user 100.

Detection of repetition of same sentence from the speaker who is trying to communicate with hearable wearing user 100 can provide a health indicator related to robustness of cognition and/or hearing of user 100. Additionally, the repetition may be a sign that the hearable 110 is not working properly and that an action should be taken, such as: performing an automated self-check of hearable 110 or providing an audible instruction to user 100 to reposition hearable 110.

When a user 100 is classified as hearing/listening, an audio analysis may be performed upon audio data captured with a microphone 217/370 to determine whether the user 100 is listening to other people speaking or to recorded audio (e.g., radio, television, or the like). The social health index or speaking/listening ratio may comprise listening to all audio, or only to specific types of sources, such as e.g., other people speaking. The speaking/listening ratio may also be combined with other indicators of social health to determine a social health index. The speaking/listening ratio may be compared with a benchmark ratio. In some embodiments, classification may be based on crowdsourcing techniques to determine the distribution of ratios of different people and what a ratio means for the social health of a user 100 compared to other users. This ratio and/or the social health index can be monitored over time to see if there are any changes. For example, the speaking/listening ratio may be compared with a previously determined ratio (e.g., month over month, year over year, or the like) for the same user 100 to determine if there has been a change (i.e., the user 100 is speaking less and thus is not as engaged as they once were). For people with health issues, for example elderly people with Alzheimer disease, monitoring of the speaking/listening ratio and/or the social health index over time may be used to monitor gradual or sudden changes of the health of the user 100.

The context of the user 100 may also be determined using sensors in the hearables 110, or in any other device in communication with the hearables (e.g., a smartphone, smart watch, computer). The determined context may then be used to set or adjust the parameters of the system. For example, it may be determined if the user 100 is in a noisy environment with many people, such as e.g., a restaurant, or having a quite private conversation. Or it may be determined that the user 100 is running, walking, or performing some other type of activity which does not lend itself to speaking. Depending upon the context and/or activity of the user 100, the classification of what constitutes speaking may be adjusted. In one embodiment, speaking determination may simply be turned off in certain contexts (e.g., noisy environment) or during certain activities (e.g., running). In another embodiment, such as a noisy environment, audio data may be disregarded, and classification may be made using motion data only. In yet another embodiment, such as a noisy environment, amplitude thresholds may be raised as a user 100 may be expected to speak louder in the noisy environment. The activities of the user may also affect the head motions and vibrations, and therefore, based on the determined context/activity, the parameters/settings of the motion analysis may be adapted. This may minimize the impact of the motion of the body on the detected motion of the head.

In some embodiments, when motion is detected by the motion sensors 350, but it is determined that the user 100 is not speaking, the motion data may be related to the user 100, eating, chewing, or drinking. These activities may be further analyzed to determine whether e.g., the user 100 is eating too fast, not chewing food enough, or speaking while eating. This can be used to detect (bad) habits and may be used to give feedback and/or notifications to the user 100. The total eating/chewing time may also be determined and used for analysis. This may be useful to a user 100 who should eat slowly or not too much because of medical conditions. It can also be determined if a user 100 eats when they should eat, if they have a regular pattern, or if they skip a meal, or have snacks at inappropriate times. Using the mandible motion and mandible vibration, alone or in combination with audio data, the type of food the user 100 is eating may also be classified such as e.g., soft, hard, or chewy.

Cranium motion 120, 130, and 140 and/or mandible motion 150 may also be used to detect if a user 100 takes a medicine they need to take (e.g., by monitoring swallowing) at the appropriate times. Movement and/or position of the mandible 103 and the cranium 102 may both be used in the analysis. For example, when swallowing pills, a user 100 normally tilts his or her cranium back while swallowing, which is easily detectable.

The discussion above shows examples of the calculation of health indicators through the use of motion sensors incorporated into hearables. Many different variations and other health indicators may be easily envisioned. They key is the analysis of the head motion, which may include determining motion and/or orientation of the cranium, and motion and/or vibrations of the mandible. One the different motions have been separated, statistical feature analysis and machine learning techniques may be applied to derive the desired health indicators.

Example Activity Classification Operations

Figure 4:
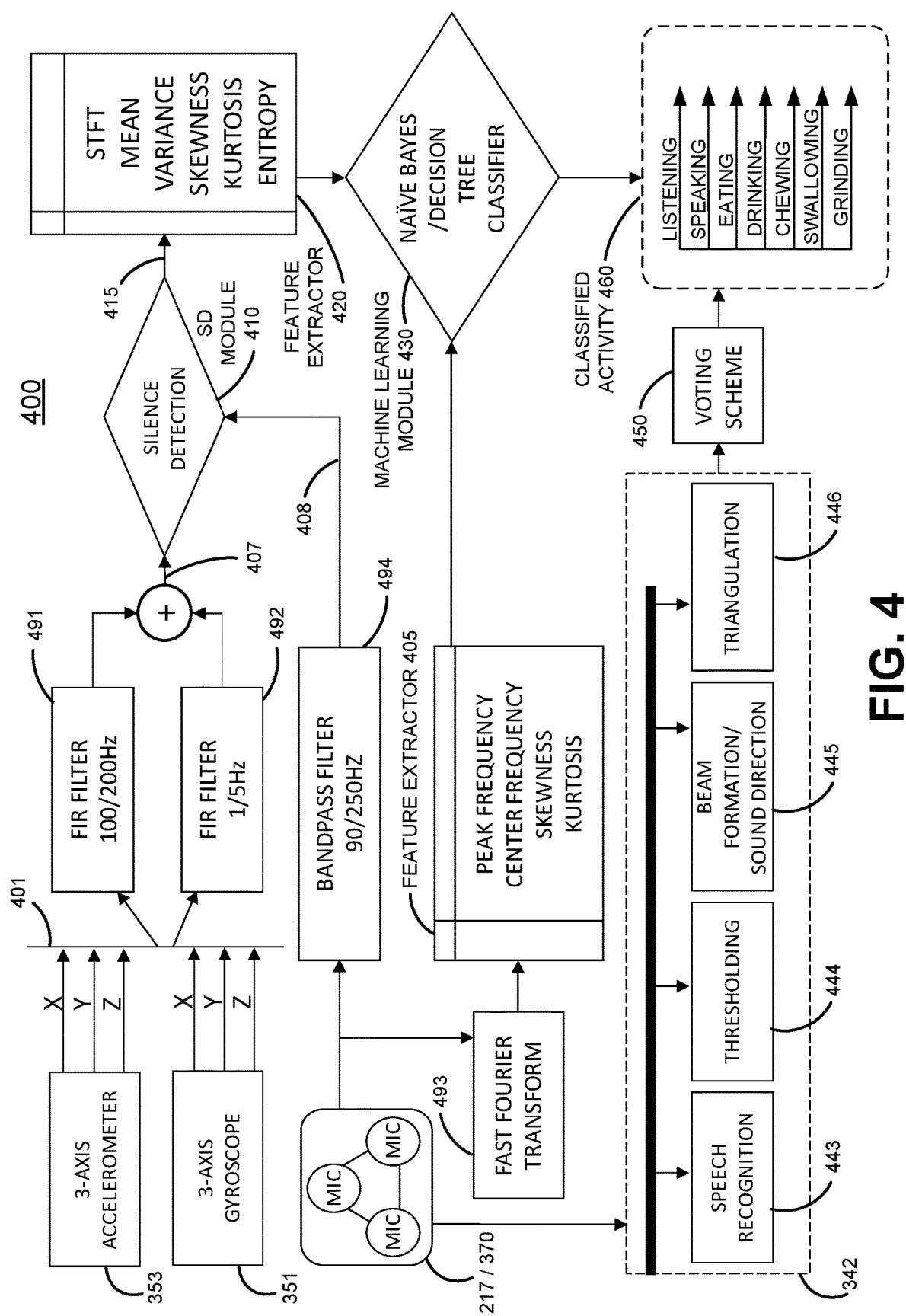
FIG. 4 illustrates a flow diagram of the operation of a hearable to classify an activity of the head of a user, in accordance with various aspects of the present disclosure

FIG. 4 illustrates a flow diagram 400 of the operation of a hearable 110 to classify an activity of the head 101 of a user 100, in accordance with various aspects of the present disclosure. In some embodiments, not all blocks and/or procedures illustrated are accomplished. That is, some may be omitted or skipped. In some embodiments, one or more blocks or procedures that are not depicted may additionally or alternatively be included. Starting at the upper left corner a three-axis accelerometer 353 of a hearable 110 acquires head motion data 401, which may be time stamped. At the substantially the same time, a three-gyroscope 351 of hearable 110 acquires head motion data 401 which may be time stamped. The head motion data 401 may then be analyzed, processed and/or filtered, to extract the motion data of interest, such as e.g., cranium motion data, mandible motion data 407 (regarding mandible movement and/or vibration). For example, as shown in FIG. 4, head motion data 401 from accelerometer 353 and gyroscope 351 are provided to FIR filter 491, which filters in the 100 to 200 Hz range to determine if mandible vibrations 160 associated with speaking by user 100 are present. Head motion data from accelerometer 353 and gyroscope 351 are also provided to FIR filter 492, which filters in the 1 to 5 Hz to determine if mandible motion 150 associated with chewing by user 100 are present. At substantially the same time as the acquisition of the head motion data 401, one or more microphones 217/370 of the hearable 110 also acquire audio data 408 which may be time stamped and provided to bandpass filter 494 where frequencies between 90 and 250 Hz are permitted to pass, as this frequency range is associated with fundamental frequencies of most adult vocal cords, and these frequencies would occur if user 100 were speaking. FIR filters 491 and 492 and bandpass filter 494 are examples of filters 390 which may be incorporated into sensor processing unit 320.

To eliminate noise from other sources, two FIR filters (491 and 492) are used due to the frequencies of speech activity and mastication differ greatly in bandwidth. Further noise isolation can be achieved by summing the spectral frequency on the fact that the signal of interest will be in the same spectral range as compared to noise which would have a spread. Accordingly, as depicted, outputs from FIR filter 491 and FIR filter 492 are summed and this mandible motion data 407 is provided as one input to silence detection module 410. A second input to silence detection module 410 is audio data 408 (which has been filtered), provided from the output of bandpass filter 494.

Silence detection module 410 may be stored in memory 340 and operated as an algorithm on sensor processor 330. If the head motion data 401 and audio data 408 are all time stamped, they may be easily synchronized before filtering and upon receipt as inputs to silence detection module 410. In some embodiments, the head motion data 401 and audio data 408 are acquired and processed at the same time with inherent synchronization. Silence detection module 410 separates voiced and silence segments in the stream of inputs which it receives. By "silence" what is meant is that there is no signal of interest in the data stream for a period of time. The root mean squared (RMS) energy of the signal from microphones 217/370 over short duration is beneficial in segmenting the portions of filtered motion data and filtered audio data which include speech by the user. The separation effected by silence detection module 410 results in maximizing information associated with speech before processing it further. The output of silence detection module 410, is a synchronized data stream 415 and is provided to feature extractor module 420. It should be appreciated that in some embodiments, silence detection module 410 may be omitted and a synchronized data stream 415 may be created from mandible motion data 407 and audio data 408 and then provided as an input to feature extractor module 420.

Feature extractor module 420 extracts one or more spectral and/or temporal features from the signal received as an input. Feature extractor module 420 may operate as a module on sensor processor 330. A short time Fourier transform (STFT) is applied to the summed signal from the gyroscope 351 and the accelerometer 353 to obtain time dependent and spectral features of the signal. In addition to spectral features, one or more temporal features such as mean, variance, skewness, kurtosis, and entropy may be determined. For example, entropy of a signal which quantifies the randomness in distribution of the signal may be useful in characterizing stochastic process. Any other features of interest may be determined, and these features of interest depend on the health indicator to be determined.

A fast Fourier transform (FFT) 493 may be used to similarly process audio data acquired from microphones 217/370. Sensor processor 330 may perform the FFT. This transformed audio data then has its features extracted by feature extractor module 405 which extracts features such as peak frequency, center frequency, skewness, and kurtosis and supplies these features to machine learning module 430.

Machine learning module 430 receives features which were extracted by the feature extractor module 420 and feature extractor module 405. Sensor processor 330 may operate machine learning module 430 as an algorithm. Machine learning module 430 applies one or more machine learning techniques such as Support Vector Machine (SVM), Hidden Markov Model (HMM), or Naive Bays with Kernel Density Estimator to detect contest of speaking, listening, or mastication. The output 460 of machine learning module 430 is a classification of the activity of the head 101 of user 100 as one or more of: listening, speaking, eating, drinking, chewing, swallowing, and/or teeth grinding. It should be appreciated machine learning module 430 may be configured to classify a greater or lesser number of activities and may classify other activities of a user's head 101, such as sleeping, snoring, sneezing, and/or coughing.

In some embodiments, audio data from microphones 217/370 can also be supplied to one or more modules 342, such as speech recognition module 443, thresholding module 444, and or beam formation/sound direction module 445. Speech recognition module 443 recognizes speech in audio data to determine if user 100 is speaking or someone is speaking to user 100. Thresholding module 444 adjusts speaker and listener amplitudes which are used as thresholds for whether or not speech is occurring. These thresholds may be adjusted based upon environmental noise and other factors such as overall activity of a user (e.g., stationary, walking, running, driving, etc.). Beam formation/sound direction module 445 uses signals from a plurality of microphones to form a beam to detect the direction from which a source of sound emanates relative to user 100. Triangulation module 446 uses signals from a plurality of microphones in a known arrangement with respect to one another to triangulate the direction/location from which a source of sound emanates relative to user 100. If motion of user 100 indicates turning toward or tracking the source of the sound, there is a high likelihood that user 100 is listening. As depicted, outputs from module(s) 342 are provided for use in a voting scheme 450 which fuses the outputs of speech, thresholding, and beam formation to improve the accuracy of the context of the environment of user 100. This context information may be supplied to machine learning module 430 and/or used to validate user activity classification outputs 460 which are made by machine learning module 430. In some embodiments, voting scheme 450 may be eliminated and outputs from modules 342 are provided as additional input to machine learning module 430.

Example Methods of Operation

FIG. 5 illustrates a flow diagram 500 of an example method of hearable use, in accordance with various aspects of the present disclosure. Procedures of this method will be described with reference to elements and/or components of one or more of FIGS. 1-4. It is appreciated that in some embodiments, the procedures may be performed in a different order than described, that some of the described procedures may not be performed, and/or that one or more additional procedures to those described may be performed. Flow diagram 500 includes some procedures that, in various embodiments, are carried out by one or more processors (e.g., processor 330, host processor 310, or the like) under the control of computer-readable and computer-executable instructions that are stored on non-transitory computer-readable storage media (e.g., host memory 311, internal memory 340, or the like). It is further appreciated that one or more procedures described in flow diagram 500 may be implemented in hardware, or a combination of hardware with firmware and/or software.

With reference to FIG. 5, at procedure 510 of flow diagram 500, in various embodiments, a sensor processor 330 of a hearable 110 acquires audio data from a microphone (e.g., a microphone 217 or 370) of a hearable 110, while the hearable 110 is disposed at least partially within an ear 104 of a user 100 of the hearable 110. The audio data may be filtered, such as with a bandpass filter centered around a frequency associated with vibrations caused by a user 100 speaking. For example, the audio filter may pass a band between 90 Hz and 250 Hz in one embodiment. The center frequency bandpass filter and width of the band passed may be preset or may be determined for a user 100 during an initialization period.

With continued reference to FIG. 5, at procedure 520 of flow diagram 500, in various embodiments, the sensor processor 330 of the hearable 110 acquires head motion data from at least one motion sensor 350 of the hearable 110. The head motion data describes motions of a head 101 of the user 100. The head 101 comprises a cranium 102 and a mandible 103. The head motion data (e.g., 401) is acquired while the hearable 110 is disposed at least partially within the ear 104 of the user 100. The head motion data comprises cranium motion data (e.g., data describing cranium motions such as motion 120, motion, 130, and motion 140) and mandible motion data (e.g., mandible motion data 407 which describes mandible movement 150 and mandible vibration 160).

With continued reference to FIG. 5, at procedure 530 of flow diagram 500, in various embodiments, the sensor processor 330 separates the mandible motion data from the head motion data. The mandible motion data includes up/down motion 150 and vibration 160. Filtering such as FIR filtering or bandpass filtering may be used to determine the vibrations 160 and/or motions 150 and separate mandible motion data from the overall head motion data. For example, a separate filter may be used on each of the frequencies associated with speaking and chewing.

With continued reference to FIG. 5, at procedure 540 of flow diagram 500, in various embodiments, the sensor processor 330 synchronizes two or more of the cranium motion data, mandible motion data, and audio data into a synchronized data stream. For example, the mandible motion data and the audio data may be synchronized into a synchronized data stream (e.g., 415). The synchronizing may be accomplished using time stamps which are associated with the different data during the capture of the data. Synchronizing may also include synchronizing data captured by two separate hearables 110. This may comprise synchronizing clocks of the two hearables or determining an offset between the clocks of the two hearables. The synchronizing may also be accomplished by capturing the sources of the data substantially at the same time and processing the sources of the data at the same time. The synchronization accuracy needed, in some embodiments, may be on the order of a second, but may be a shorter or longer span of time in other embodiments. The required synchronization may depend on the health indicator to be determined and may, as such, be adapted to the application.

With continued reference to FIG. 5, at procedure 550 of flow diagram 500, in various embodiments, the sensor processor 330 classifies an activity of the head 101 during a portion of the synchronized data stream. In some embodiments, the activity may be classified as one or more of listening, speaking, eating, drinking, chewing, swallowing, and teeth grinding. Based on the filtering of the motion data, the motion data alone may be used to determine whether the user 100 is speaking or not speaking. For example, if a filtered frequency range of mandible vibration 160 associated with speaking exceeds an amplitude threshold, the user 100 is classified as speaking. Likewise, the filtered audio data may be used alone to classify whether the user 100 is speaking or not speaking. For example, if a filtered frequency range of audio data associated with speaking exceeds an amplitude threshold, the user 100 is classified as speaking. In some embodiments, both the filtered audio data and the filtered mandible motion for a synchronized period of time are used together to determine if a user 100 is speaking or not speaking. For example, if both the audio data and motion data exceed thresholds associated with speaking, the user 100 is classified as speaking. If not, the user is classified as not speaking (e.g., as listening). The different activities that can be determined depend on the quality and accuracy of the motion data and the applied processing and filtering, and this may depend on the user, the hearable, and/or the context. The activities that can be reliably determined may be decided based on the machine learning.

In some embodiments, the classifying is adjusted based on context of an overall activity being performed by the user 100. The context of the user 100 may also be determined using sensors in the hearables 110, or in any other device in communication with the hearables (e.g., a smartphone, smart watch, computer). For example, it may be determined if the user 100 is in a noisy environment with many people, such as e.g., a restaurant, or having a quite private conversation. Or it may be determined that the user 100 is running, walking, or performing some other type of activity which does not lend itself to speaking. Depending upon the context and/or activity of the user 100, the classification of what constitutes speaking may be adjusted. In one embodiment, speaking determination may simply be turned off in certain contexts (e.g., noisy environment) or during certain activities (e.g., running). In another embodiment, such as a noisy environment, audio data may be disregarded, and classification may be made using motion data only. In yet another embodiment, such as a noisy environment, amplitude thresholds may be raised as a user 100 may be expected to speak louder in the noisy environment.

With continued reference to FIG. 5, at procedure 560 of flow diagram 500, in various embodiments, the sensor processor 330 generates a health indicator for the user 100 based on the activity and the synchronized data stream.

In some embodiments, the health indicator may be an instantaneous health indicator associated with the portion of the synchronized data stream. That is, it may be calculated immediately or at some other time for the instance of time represented by the portion of the synchronized data stream. For example, this may comprise filtering the portion of the synchronized data stream to determine a first amount of time attributed to speaking by the user and a second amount of time attributed to listening by the user, and then determining a ratio between the first amount of time and the second amount of time. As previously discussed, an instantaneous health indicator is for a single time period or a shorter interval than a cumulative health indicator.

In some embodiments, the health indicator may be a cumulative health indicator associated with a plurality of instances of the activity by the user. For example, a plurality of instances of speaking or not speaking. The cumulative health indicator may indicate a speaking/listening ratio over a period than an instantaneous health indicator and/or may comprise a cumulation of the data of two or more instantaneous health indicators.

Conclusion

The examples set forth herein were presented in order to best explain, to describe particular applications, and to thereby enable those skilled in the art to make and use embodiments of the described examples. However, those skilled in the art will recognize that the foregoing description and examples have been presented for the purposes of illustration and example only. The description as set forth is not intended to be exhaustive or to limit the embodiments to the precise form disclosed. Rather, the specific features and acts described above are disclosed as example forms of implementing the claims.

Reference throughout this document to "one embodiment," "certain embodiments," "an embodiment," "various embodiments," "some embodiments," or similar term means that a particular feature, structure, or characteristic described in connection with the embodiment is included in at least one embodiment. Thus, the appearances of such phrases in various places throughout this specification are not necessarily all referring to the same embodiment. Furthermore, the particular features, structures, or characteristics of any embodiment may be combined in any suitable manner with one or more other features, structures, or characteristics of one or more other embodiments without limitation.

What is claimed is:

1. A hearable comprising:
a wearable structure at least a portion of which is configured to be disposed within an ear of a user of a hearable;
at least one microphone coupled with the wearable structure; and
a sensor processing unit disposed within the wearable structure and communicatively coupled with the at least one microphone, the sensor processing unit configured to:
acquire, by the sensor processing unit, audio data from the at least one microphone of the hearable;
acquire, by the sensor processing unit, head motion data from at least one motion sensor of the sensor processing unit, wherein the head motion data describes motions of a head of the user, wherein the head comprises a cranium and a mandible, and wherein the head motion data comprises cranium motion data and mandible motion data;
separate, by the sensor processing unit, the mandible motion data from the head motion data by band pass filtering the head motion data on a frequency range of mandible vibrations associated with speaking to separate the mandible motion data from the head motion data;
synchronize, by the sensor processing unit, the mandible motion data and the audio data into a synchronized data stream;
classify, by the sensor processing unit, an activity of the head during a portion of the synchronized data stream; and
generate, by the sensor processing unit, a health indicator for the user based on the activity and the synchronized data stream, wherein the health indicator is used to monitor an aspect of health of the user.

2. The hearable of claim 1, wherein the sensor processing unit is further configured to:
adjust, by the sensor processor, the classifying by disregarding the audio data and using only the mandible motion data to classify the activity of the head in response to determining the user is in a noisy environment.

3. The hearable of claim 1, wherein the mandible motion data comprises at least one of a vibration of the mandible and a movement of the mandible.

4. The hearable of claim 1, wherein the sensor processing unit is configured to:
classify the activity of the head based upon a frequency filtering analysis of the synchronized data stream.

5. The hearable of claim 1, wherein the activity comprises one of listening, speaking, eating, drinking, chewing, swallowing, and teeth grinding.

6. The hearable of claim 1, wherein the health indicator comprises:
an instantaneous health indicator associated with the portion of the synchronized data stream.

7. The hearable of claim 6, wherein the instantaneous health indicator comprises a speaking versus listening ratio and the sensor processing unit is configured to:
filter the portion of the synchronized data stream to determine a first amount of time attributed to speaking by the user and a second amount of time attributed to listening by the user; and
determine a ratio between the first amount of time and the second amount of time.

8. The hearable of claim 1, wherein the health indicator comprises:
a cumulative health indicator associated with a plurality of instances of the activity by the user.

9. A sensor processing unit comprising:
a memory;
at least one motion sensor; and
a sensor processor coupled with the memory and the at least one motion sensor, wherein the sensor processor is configured to:
acquire, by the sensor processor, audio data from at least one microphone of a hearable while the hearable is worn disposed at least partially within an ear of a user of the hearable;
acquire, by the sensor processor, head motion data from the at least one motion sensor of the sensor processing unit, wherein the head motion data describes motions of a head of the user, wherein the head comprises a cranium and a mandible, and wherein the head motion data comprises cranium motion data and mandible motion data;
separate, by the sensor processor, the mandible motion data from the head motion data by band pass filtering the head motion data on a frequency range of mandible vibrations associated with speaking to separate the mandible motion data from the head motion data;
synchronize, by the sensor processor, the mandible motion data and the audio data into a synchronized data stream;
classify, by the sensor processor, an activity of the head during a portion of the synchronized data stream; and
generate, by the sensor processor, a health indicator for the user based on the activity and the synchronized data stream, wherein the health indicator is used to monitor an aspect of health of the user.

10. The sensor processing unit of claim 9, further comprising:
the at least one microphone.

11. The sensor processing unit of claim 9, wherein the sensor processing unit is further configured to:
adjust the classifying by turning off a speaking determination aspect of the classifying the activity of the head in response to determining the user is walking or running.

12. The sensor processing unit of claim 9, wherein the mandible motion data comprises at least one of a vibration of the mandible and a movement of the mandible.

13. The sensor processing unit of claim 9, wherein the sensor processing unit is configured to:
classify the activity of the head based upon a frequency filtering analysis of the synchronized data stream.

14. The sensor processing unit of claim 9, wherein the activity comprises one of listening, speaking, eating, drinking, chewing, swallowing, and teeth grinding.

15. The sensor processing unit of claim 9, wherein the health indicator comprises:
an instantaneous health indicator associated with the portion of the synchronized data stream.

16. The sensor processing unit of claim 15, wherein the instantaneous health indicator comprises a speaking versus listening ratio and the sensor processor is configured to:
filter the portion of the synchronized data stream to determine a first amount of time attributed to speaking by the user and a second amount of time attributed to listening by the user; and
determine a ratio between the first amount of time and the second amount of time.

17. The sensor processing unit of claim 9, wherein the health indicator comprises:
a cumulative health indicator associated with a plurality of instances of the activity by the user.

18. A method of hearable use, the method comprising:
acquiring, by a sensor processor of a hearable, audio data from a microphone of a hearable while the hearable is disposed at least partially within an ear of a user of the hearable;
acquiring, by the sensor processor of the hearable, head motion data from at least one motion sensor of the hearable while the hearable is disposed at least partially within the ear of the user, wherein the head motion data describes motions of a head of the user, wherein the head comprises a cranium and a mandible, and the head motion data comprises cranium motion data and mandible motion data;
separating, by the sensor processor, the mandible motion data from the head motion data by band pass filtering the head motion data on a frequency range of mandible vibrations associated with speaking to separate the mandible motion data from the head motion data;
synchronizing, by the sensor processor, the mandible motion data and the audio data into a synchronized data stream;
classifying, by the sensor processor, an activity of the head during a portion of the synchronized data stream; and
generating, by the sensor processor, a health indicator for the user based on the activity and the synchronized data stream, wherein the health indicator is used to monitor an aspect of health of the user.

19. The method as recited in claim 18, wherein the separating the head motion data into cranium motion data and mandible motion data further comprises:
determining, from the mandible motion data, a vibration of the mandible.

20. The method as recited in claim 18, wherein the separating the head motion data into cranium motion data and mandible motion data further comprises:
determining, from the mandible motion data, a movement of the mandible.

21. The method as recited in claim 18, wherein the classifying an activity of the head during a portion of the synchronized data stream comprises:
classifying the activity as one of listening, speaking, eating, drinking, chewing, swallowing, and teeth grinding.

22. The method as recited in claim 18, wherein the classifying is adjusted by turning off a speaking determination aspect of the classifying the activity of the head in response to determining the user is in a noisy environment.

23. The method as recited in claim 18, wherein the generating a health indicator for the user based on the synchronized data stream and the activity comprises:
generating an instantaneous health indicator associated with the portion of the synchronized data stream.

24. The method as recited in claim 23, wherein the instantaneous health indicator comprises a speaking versus listening ratio calculated by the sensor processor by:
filtering the portion of the synchronized data stream to determine a first amount of time attributed to speaking by the user and a second amount of time attributed to listening by the user; and
determining a ratio between the first amount of time and the second amount of time.

25. The method as recited in claim 18, wherein the generating a health indicator for the user based on the synchronized data stream and the activity comprises:
generating a cumulative health indicator associated with a plurality of instances of the activity by the user.

* * * * *